350-418 SR

XR 4,148,565

United Stat

Gunst

[11] 4,148,565

[45] Apr. 10, 1979

[54] OPTICAL TRAINING DEVICE

[76] Inventor: Ole Gunst, 19475 Grandview Dr., Topanga, Calif. 90290

[21] Appl. No.: 804,993

[22] Filed: Jun. 9, 1977

[51] Int. Cl.[2] .......................... A61B 3/00; A61H 5/00

[52] U.S. Cl. ...................................... 351/2; 128/25 A; 128/76.5; 350/179

[58] Field of Search .................... 351/2; 350/179, 319; 128/76.5, 25 A

[56] References Cited

U.S. PATENT DOCUMENTS

| | | | |
|---|---|---|---|
| 695,606 | 3/1902 | Grun | 350/179 |
| 3,875,934 | 4/1975 | Sadanaga | 351/2 X |

*Primary Examiner*—Paul A. Sacher
*Attorney, Agent, or Firm*—Henry M. Bissell

[57] ABSTRACT

An optical device comprising a pair of lenses mounted along a viewing axis within a housing and angularly adjustable relative to the viewing axis by a manipulator extending outside the housing. The manipulator comprises an exterior knob on a shaft extending through the housing and having a gear engaging corresponding sector gear portions of individual pivoted mounts supporting the respective lenses. A flexible, preferably elastic membrane, sealed to the respective lenses and extending therebetween, contains a fluid such as glycerine, having an index of refraction corresponding to the refractive index of the lens material. Adjustment of the manipulator knob jointly varies the angles of the respective lenses relative to the viewing axis and to each other so as to shift the direction of light transmitted through the device. The device is used by an individual in exercising eye muscles to correct a condition of squint, e.g., the cross-eyed condition not infrequently encountered in young children.

11 Claims, 5 Drawing Figures

OPTICAL TRAINING DEVICE

BACKGROUND OF THE INVENTION

1. Field of the Invention

This invention relates to optical devices and, more particularly, to such devices as may be employed in exercising or training the eye muscles.

2. Description of the Prior Art

In human beings, it is the function of using two eyes together that keeps the optical axes straight in a normal person. Without normal muscular control, for example in the case where one eye becomes blind, that eye may tend to revert to an anatomical position of rest in line with the axis of the orbit, which causes it to appear to be diverging. The visual axes can remain straight only if each eye has reasonably good vision, the ocular muscles can move the eyes in the required direction of gaze, and the complex neuromuscular reflexes required to coordinate the movements of the two eyes are intact. Failure to maintain the visual axes parallel may therefore result from a visual defect in one or both eyes, a muscular defect resulting in loss of normal movement of the eye, or a defect in the central nervous system involving the coordinating nervous pathways.

A true squint is a condition in which the visual axes are no longer parallel. Clinically, squints are divided into concomitant and paralytic types. In the first type, the abnormal angle between the visual axes remains constant in all positions of gaze, whereas in the latter type, the angle of squint varies with the direction of gaze. The commonest type of squint is the convergent concomitant type seen in small children who are consistently or intermittently cross-eyed.

To view objects close by, the visual axes must converge, so that both eyes can view the same object, and the focus of the eye must be adjusted for near vision. The link between convergence of the eyes and focusing, or accommodation, is very strong and normally the two actions work in harmony. Most small children are far-sighted, which means that in order to see clearly close to, they have to exert an extra amount of accommodative effort. As accommodation and convergence are closely linked, the extra effort of accommodation tends to produce an overconvergence; but, provided that the visual acuity of each eye is normal and the motor control of the eyes is normal, this tendency is controlled. However, if the vision of one eye is reduced, for example by disease or an error of refraction, binocular vision breaks down and overconvergence occurs. Sometimes convergent concomitance is precipitated in young children by a systemic disease such as measles, or there may be a family history of squint.

Once parallelism of the visual axes is lost, the image of objects no longer lies on a familar area or retina, and instead of the images from the two eyes being fused into one, two images are perceived. This condition of double vision, or diplopia, is intolerable to the child, who reacts by "suppressing" the image from the squinting eye. If the suppression is allowed to continue, the central vision of the affected eye drops rapidly to a low level, so that even if the original disturbances that started the squint is corrected, this loss of vision, or amblyopia, of the squinting eye will prevent the restoration of normal binocular vision and thus perpetuate the squint. The longer the suppression is allowed to continue, the less likely is the child to regain normal vision in the squinting eye. Covering the good eye generally encourages the recovery of the suppressed vision, but to be effective it must be started as soon as the squint is noticed. Retraining of the binocular reflexes can be aided by special exercises.

In contrast, many people do not have the perfect balance of accommodation and convergence that enables the movements of the two eyes to bring the visual axes to the point of focus for all distances of vision. In such cases, the eyes may tend to converge or diverge too much for a given distance, a condition known as heterophoria.

While special mechanism having adjustable lenses has been developed for use by optometrists and other specialists, these devices are usually costly and relatively cumbersome and are not suitable for use in the home by the individual patient. Home training and exercise aids for correcting squint are generally limited to an opaque lens or sheet for covering one eye or to exercises, such as concentrating one's vision on one's fingertip while moving it toward or away from one's face. What is needed is a simple, lightweight, portable, inexpensive device which includes a lens system comparable to those employed for the purpose in a specialist's office but which is feasible for purchase and use by the individual patient in his habitual environment, such as the home or office.

SUMMARY OF THE INVENTION

In brief, arrangements in accordance with the present invention comprise a pair of lenses pivotably mounted within a housing and having a cell of fluid of comparable refractive index between them. A single pivotable lens may be employed in conjunction with a fixed lens, but the dual pivotable arrangement is preferred. An external knob on a shaft coupled by a gearing arrangement to engage the pivotable lens mounts serves to adjust the angles of the lenses so that the path of a light image through the device may be controlled. The transparent fluid is contained within a flexible, elastic membrane sealably joined to the respective lenses at opposite ends thereof.

In using an embodiment of the invention as described. the individual holds it to the eye needing the corrective exercise and directs his gaze from both eyes to a noticeable point on the opposite wall, perhaps ten or fifteen feet distant. He then adjusts the manipulator knob until the images seen by the two eyes are superimposed in his brain. Thereafter, he turns the manipulator knob to cause the image seen through the device to move in a direction to compensate for his condition of squint, while trying to make the muscles move the eye to follow the diverted image. He continues diverting the image in this fashion as far as he can, thus exercising the eye muscles to correct the squint condition. For example, if the user is cross-eyed, he begins with the exercise device adjusted to produce a diverging beam effect for light passing through the device. Then while looking through the device, he adjusts the manipulator to tend to straighten out the light path through the device which, if followed by his eye direction, tends to uncross his eyes. An opposite control would be exerted by an individual having a wall-eyed condition. The device is simple to use and is effective in correcting the conditions described.

In one particular arrangement in accordance with the invention, the lenses are glass and are mounted in a plastic holder with a generally cylindrically-shaped membrane extending between the two lenses and having its opposite ends sealingly affixed to the respective lens peripheries. In order that the device may operate effectively through varying angles of pivot of the lenses relative to the axis of the housing, the fluid-containing membrane and lenses are squeezed close together in the mounting elements, thus expanding the membrane and avoiding any wrinkles which might otherwise be formed therein from pivoting of the lenses and their holders.

In another particular arrangement, the fluid between the lenses is contained in a sealed transparent membrane comprising a cell which is then longitudinally compressed between the two lenses. In another particular arrangement in accordance with the invention, the lenses are integrally formed as part of the respective pivotable mounting elements, the elements being formed of acrylic and thereafter polished and finished to the desired flatness so as to develop desirable optical properties.

BRIEF DESCRIPTION OF THE DRAWING

A better understanding of the present invention may be had from a consideration of the following detailed description, taken in conjunction with the accompanying drawing in which.

DESCRIPTION OF THE PREFERRED EMBODIMENTS

Figure 1:
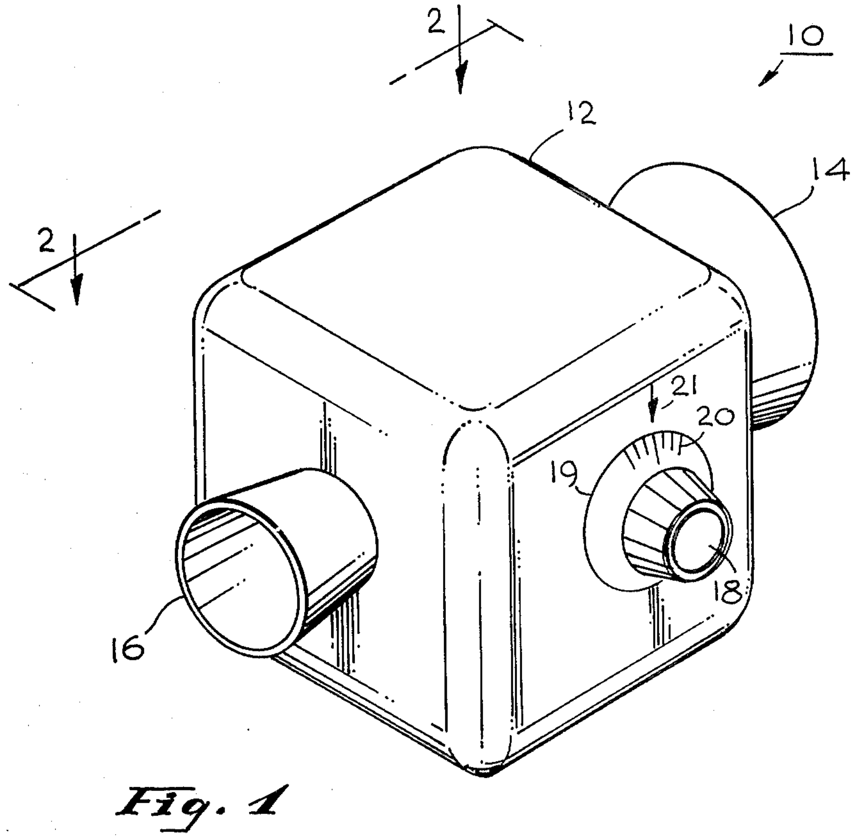
FIG. 1 is a perspective view of one particular arrangement in accordance with the invention.
Figure 2:
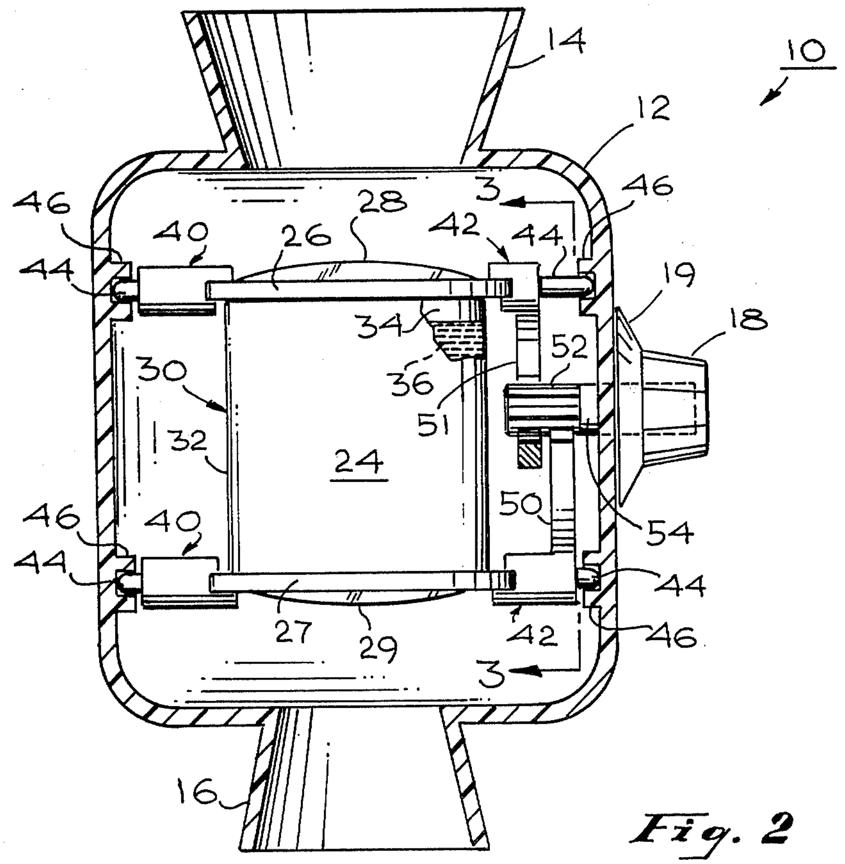
FIG. 2 is a sectional view of the arrangement of FIG. 1, taken along the plane 2—2 and looking in the direction of the arrows.

As particularly shown in FIGS. 1 and 2, one particular arrangement 10 in accordance with the present invention comprises an exterior housing 12 on which are mounted a light shade 14, an eyepiece 16, and an adjustment knob 18. The knob 18 may be provided with a skirt 19 bearing calibration marks 20 opposite a reference mark 21 on the adjacent face of the housing 12. The housing 12 is generally cube-shaped and supports the light shade 14 and eyepiece 16 on opposite faces in optical alignment.

Within the housing 12 in optical alignment with the light shade 14 and eyepiece 16 is a pivotable lens mounting arrangement 24 which is coupled by gearing to the knob 18. As shown in FIG. 2, the lens mounting arrangement comprises a pair of lens mounts 26 and 27 supporting respective half-convex lenses 28 and 29 in opposed relationship and a liquid cell 30 between the lens mounts 26, 27. As shown in FIG. 2, the cell 30 comprises a membrane 32 affixed in sealing relationship to inwardly facing rims of the lens mounts, such as the rim 34. The configuration of the membrane 32 is generally cylindrical and its interior space is filled with a liquid 36 which is selected to have an index of refraction very close to the index of refraction of the material of the lenses 28, 29.

Each of the lens mounts 26, 27 is supported between an associated pair of pivot members 40, 42. Each pivot member 40, 42 includes in turn a pivot pin 44 located within the bore of a corresponding support member 46 affixed to or formed as part of the interior wall of the housing 12.

Figure 3:
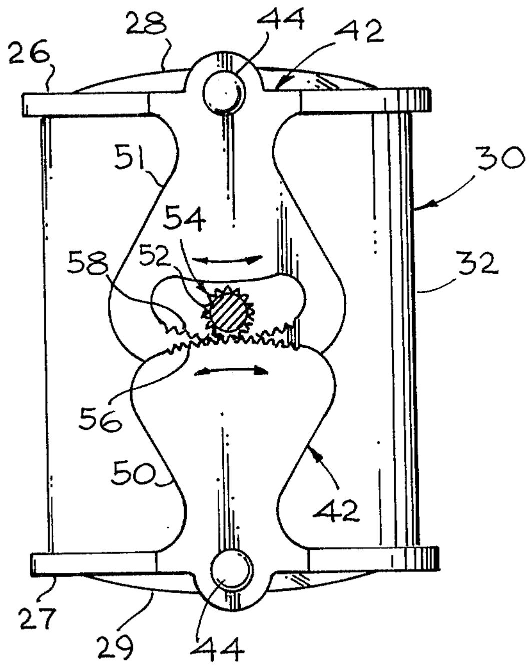
FIG. 3 is a sectional view of a portion of the device of FIGS. 1 and 2, taken along the line 3—3 of FIG. 2.

In addition, those pivot members 42 adjacent the knob 18 include respective sector gear arms 50, 51 which are coupled to a toothed gear portion 52 of a shaft 54 on which the knob 18 is mounted. As shown in further detail in FIG. 3, the sector gear arm 50 has an external gear section 56 while the opposite sector gear arm 51 has an interior toothed section 58, both of which engage the toothed portion 52 of the gear shaft 54. With this gear arrangement as shown in FIG. 3, a movement of both of the arms 50, 51 in the same direction results when the gear shaft 54 is rotated. For example, rotation of the gear shaft 54 in the counterclockwise direction results in movement of the arms 50, 51 to the right. This in turn causes the lens mount 26 and lens 28 to pivot in the counterclockwise direction about the pivot pin 44, while the lens mount 27 and lens 29 pivot in the clockwise direction about their associated pivot pins 44.

If desired for simplicity, one of the lens mounts 26 or 27 with its associated lens 28 or 29 may be fixed in position with only the other one being pivotably mounted and coupled to the gear shaft 54 for adjustment of the lens angle. However, the compound gear coupling shown in FIG. 3 results in double the change of angular deviation of the opposite faces of the lenses 28, 29 for a given rotation of the gear shaft 54, thus providing a greater diversion of the light image passing through the lenses 28, 29 when the lenses are set at an angle other than parallel with respect to each other. In addition, the compound gear arrangement provides a balanced deflection of the light image, since the total deflection angle is divided between the two lenses 28, 29.

Figure 4:
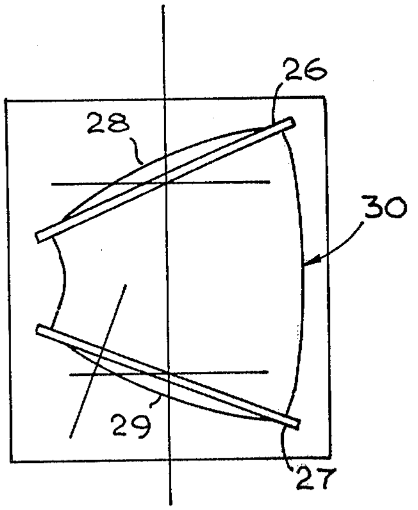
FIG. 4 is a schematic plan view of the lens arrangement of the device of FIGS. 1 and 2.

The schematic diagram of FIG. 4 illustrates the operation of arrangements in accordance with the present invention. If the lenses 28, 29 are positioned precisely parallel to each other, a light beam entering from the top passes straight through the lens system without deviation. However, if the lenses 28, 29 are pivoted so as to be at an angle with respect to each other, for example as shown in FIG. 4, a light beam coming from the top will be deflected to the right as it passes through the lens 28 and then to the left as it passes through the lens 29. The result to an observer is in impression that the object viewed is located to the left of its true position. The degree of apparent deviation from its true position can be adjustably controlled by rotating the knob 18 to vary the angle of deviation of the lenses 28, 29 from their positions of parallelism.

In use, a person wishing to exercise his eye muscles to correct a squint condition holds the device 10 of the present invention in the attitude shown in FIG. 2, placing his eye needing correction against the eyepiece 16. He then looks at some object perhaps 15 feet distant, viewing it directly with his good eye and through the device 10 with the eye needing correction. The knob 18 is then adjusted until the individual images viewed by the two eyes of the patient using the device are viewed normally for that patient. This means that the lenses 28, 29 will be at some angle other than parallel. For a person who is cross-eyed, for example, and who is holding the device 10 for viewing with his left eye, the lenses 28, 29 will be oriented as shown in FIG. 4, although the degree of deviation from parallelism will vary with the condition of the individual patient. Once the two images are superimposed within the patient's brain, the knob 18 is slowly turned to move the lenses 28, 29 toward the position of parallelism. At the same time, the patient using the device concentrates on maintaining the light images superimposed in his brain's optical centers. This forces the eye muscles of the defective eye to try to move that eye into alignment with the other eye for normal vision. The patient continues to concentrate in this fashion as the knob 18 is turned to bring the lenses 28, 29 into parallelism for as long as he is able to maintain the images superimposed in his brain. When the images slip out of super-position, the process is repeated and exercising of the eye muscles in this fashion can continue for a period of time, such as 10 or 15 minutes, repeated at regular intervals, thus tending to train the eye muscles to develop normal visual control.

For a person who has a so-called "wall-eyed" condition, the device can be used with the lenses initially tilted in the opposite direction from that shown in FIG. 4 and gradually rotated in the opposite direction to that described above to bring them toward a condition of parallelism. Alternatively, the lenses can be started in positions parallel to each other and slowly rotated into an angle which develops the desired deviation of the light image as it passes through the lenses 28, 29 within the device 10.

Figure 5:
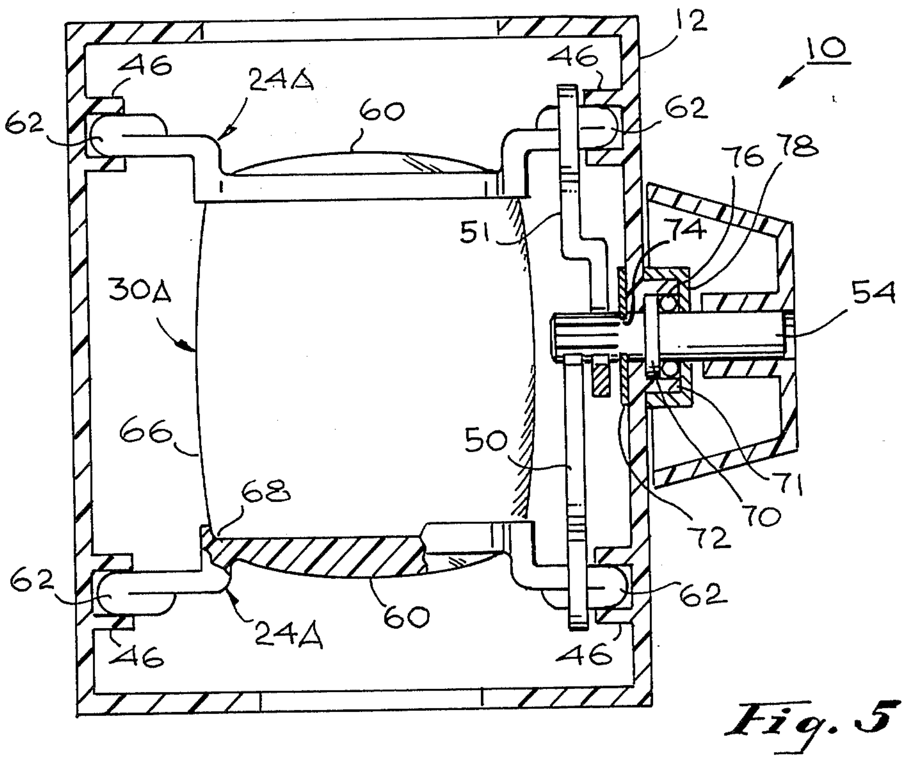
FIG. 5 is a sectional view of an alternative arrangement in accordance with the invention, showing particular details thereof.

In the alternative arrangement of FIG. 5 in which corresponding elements have been given the same designation as those in FIGS. 1–3, the housing 12 of the device 10 includes a pair of pivotable lens mounts 24A between which is supported a liquid cell 30A. Each pivotable mount 24A comprises an integral lens 60 and pivot members 62. As shown in FIG. 5, the lens mount assembly 24A is very readily formed of a single piece of clear plastic in which the pivot members 62 are formed by folding and rounding the ends of the mount 24A back on themselves. The lens 60 may be formed and polished to the desired shape and surface condition.

The liquid cell 30A is a sealed membrane 66, somewhat barrel-shaped, and containing a liquid having the same index of refraction as that of the lenses 60. The cell 30A is supported between the lens mount assembly 24A by being squeezed between them and held within inwardly directed cup shaped portions 68.

Also as shown in FIG. 5, the gear shaft 54 has an outwardly extending ring or shoulder 70 which bears against the outer surface of the housing 12 within a well 71. The shaft 54 is retained in position by a retainer washer 72 which is slipped into a pair of opposed slots 74 on the shaft 54. An O-ring 76 is mounted within the well 71 outwardly of the ring 70 and is held in position by a cover 78 which is pressed over the well 71 and held by a friction fit. Gear arms 50 and 51, similar to those shown in FIG. 2, provide the desired coupling between the gear shaft 54 and the pivotable lens supports 24A. The operation of the device of FIG. 5 is the same as that described with respect to FIGS. 1–3.

Devices in accordance with the present invention provide an extremely simple, effective, reliable and economical means of exercising the muscles associated with a defective eye squint condition to correct or eliminate that condition. Because the device is simple to use and economical in price, it can be readily provided to an individual patient for use in his home or anywhere at his convenience without having to go to a doctor's office or some center for correction of visual defects to practice the appropriate exercises. Its manipulation is readily understood and can be taught to almost any patient without difficulty. The nature of the device is such that its use can be made a sort of game for children, for example, who are very often most in need of the use of such a device to correct and strengthen their eye muscles.

Although particular arrangements of an optical training device in accordance with the present invention have been described hereinabove and shown in the accompanying drawings for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the appended claims.

What is claimed is:

1. An optical training device comprising:

a housing;

means defining an optical path through the housing including first and second lenses mounted in optical alignment within the housing;

a sealed cell positioned between the lenses and in contact therewith, the cell containing a liquid having an index of refraction approximately equal to that of the lenses;

means for permitting viewing of an external object through the lenses and the housing by one eye while the object is viewed directly outside the housing with the other eye; and means for selectively varying the plane of one of the lenses relative to the other to vary the optical path through the housing.

2. The device of claim 1 wherein the last-mentioned means comprises a rotatable shaft extending through the housing to be manipulatable by a user of the device, and gear means coupling the shaft to said one lens for selectively varying the plane thereof.

3. The device of claim 2 wherein the gear means comprises a toothed portion on the shaft coupled to a sector gear member connected to said one lens.

4. The device of claim 2 wherein the first and second lenses are both pivotably mounted within the housing for rotation relative to the housing and to each other, and wherein the gear means comprises a toothed portion of the shaft and sector gear portions of lever arms connected respectively to the first and second lenses, the sector gear portions being intercoupled with the shaft gear.

5. The device of claim 4 wherein the sector gear portion of the lever arm connected to the first lens is an external gear portion and the sector gear portion of the lever arm connected to the second lens is an internal gear portion.

6. The device of claim 1 wherein the sealed cell comprises a generally cylindrical membrane sealingly connected to respective rim portions of the first and second lenses, the space within the membrane being substantially filled with said liquid.

7. The device of claim 1 further comprising first and second pivotable lens mounts supporting the first and second lenses respectively, each of said mounts having a circular rim extending in the direction of the other mount, and wherein the sealed cell comprises a generally cylindrical membrane adhesively affixed at opposing ends to the respective rims of the first and second mounts.

8. The device of claim 7 further including opposed pivot members affixed to the lens mounts and supported within the bore of support members mounted on the interior wall of the housing.

9. The device of claim 1 wherein the first and second lenses are integrally mounted in respective first and second lens mounts, each mount including a pair of opposed pivot pins pivotally supported within corresponding protrusions extending inwardly from the housing and a cup-shaped portion for receiving said cell therein.

10. The device of claim 9 wherein the sealed cell is sealingly formed and is supported between the first and second lenses with its respective ends positioned in the cup-shaped portions.

11. The device of claim 9 wherein the pivot members comprise an extension of the associated lens mount, folded back upon themselves and rounded to fit within support members mounted interiorly of the housing.

* * * * *